United States Patent
Joshi et al.

(10) Patent No.: US 7,312,329 B2
(45) Date of Patent: Dec. 25, 2007

(54) PROCESS FOR THE PREPARATION OF PYRIMIDINE DERIVATIVES

(75) Inventors: Narendra Joshi, Navi Mumbai (IN); Shekhar Bhaskar Bhirud, Navi Mumbai (IN); Batchu Chandrasekhar, Navi Mumbai (IN); K. Eswara Rao, Navi Mumbai (IN); Subhash Damle, Thane Dist. (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 619 days.

(21) Appl. No.: 11/004,755

(22) Filed: Dec. 3, 2004

(65) Prior Publication Data

US 2005/0124639 A1 Jun. 9, 2005

Related U.S. Application Data

(60) Provisional application No. 60/561,732, filed on Apr. 13, 2004.

(30) Foreign Application Priority Data

Dec. 4, 2003 (IN) .................. 1244/MUM/2003

(51) Int. Cl.
*C07F 9/02* (2006.01)
*C07D 239/02* (2006.01)

(52) U.S. Cl. ............ 544/243; 544/315; 544/322; 544/330

(58) Field of Classification Search ............... None
See application file for complete search history.

(56) References Cited

U.S. PATENT DOCUMENTS 5,260,440 A 11/1993 Hirai et al.

FOREIGN PATENT DOCUMENTS

WO WO 03/087112 10/2003
WO WO 2004/103977 * 12/2004

OTHER PUBLICATIONS

Beck et al. "Synthesis and Biological Activity of New HMG-CoA Reductase Inhibitors. 1. Lactones of Pyridine- and Pyrimidine-Substituted 3,5-Dihydroxy-6-heptonoic (-heptanoic) Acids", *J. Med. Chem.*, 1999, 33, 52-60.

\* cited by examiner

Primary Examiner—Zachary C. Tucker
Assistant Examiner—Erich Leeser
(74) Attorney, Agent, or Firm—M. Carmen & Associates, PLLC

(57) ABSTRACT

An improved process for the preparation of pyrimidine derivatives is provided comprising reacting a Wittig reagent of the general formula

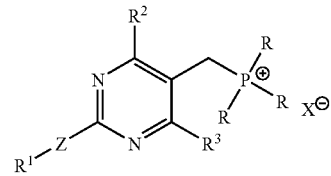

wherein R is an alkyl of from 1 to 10 carbon atoms, aryl or arylalkyl, $R^1$ is a substituted or unsubstituted hydrocarbon group, $R^2$ and $R^3$ are the same or different and are hydrogen or a substituted or unsubstituted hydrocarbon group; Z is sulfur, oxygen, sulfonyl, or imino which may be substituted by formyl, acetyl, propionyl, butyryl, isobutyryl, valeryl, isovaleryl, amino substituted by sulfonyl or alkylsulfonyl, and sulfonyl substituted by alkyl, amino or alkylamino and X is a halogen; with an aldehyde of the general formula

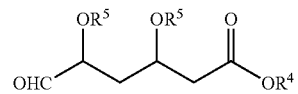

wherein $R^4$ is hydrogen, a lower alkyl or a cation capable of forming a non-toxic pharmaceutically acceptable salt and each $R^5$ are the same or different and are hydrogen or a hydrolyzable protecting group, or each $R^5$, together with the oxygen atom to which each is bonded, form a hydrolyzable cyclic protecting group, or each $R^5$ is bonded to the same substituent which is bonded to each oxygen atom to form a hydrolyzable protecting group; in the presence of a base.

55 Claims, No Drawings

PROCESS FOR THE PREPARATION OF PYRIMIDINE DERIVATIVES

PRIORITY

This application claims the benefit under 35 U.S.C. §119 to Provisional Application No. 60/561,732, filed Apr. 13, 2004 and entitled "PROCESS FOR THE PREPARATION OF RUSUVASTATIN", and from Indian Provisional Application 1244/Mum/2003, filed on Dec. 4, 2003, the contents of which are incorporated by reference herein.

BACKGROUND OF THE INVENTION

1. Technical Field

The present invention generally relates to an improved process for the preparation of pyrimidine derivatives such as 3-hydroxy-3-methylglutaryl-coenzyme A (HMG-CoA) inhibitors and their intermediates. More specifically, the present invention relates to an improved process for the preparation of rosuvastatin and its intermediates using Wittig reagents.

2. Description of the Related Art

The present invention is directed to an improved process for the preparation of pyrimidine derivatives such as rosuvastatin (also known as bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid]). Rosuvastatin has the following structural formula I:

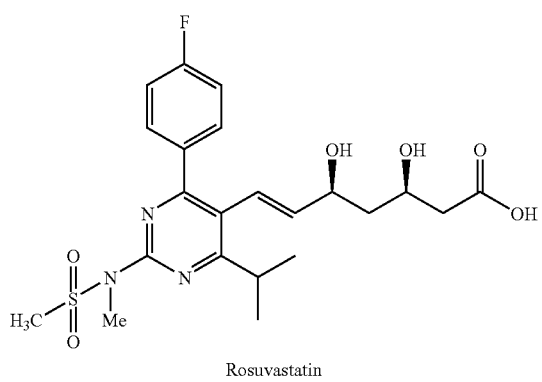

Rosuvastatin

Generally, rosuvastatin is a synthetic lipid-lowering agent that acts as an inhibitor of 3-hydroxy-3-methylglutaryl-coenzyme A (HMG-CoA) reductase (HMG-CoA Reductase inhibitor). This enzyme catalyzes the conversion of HMG-CoA to mevalonate, an early and rate-limiting step in cholesterol biosynthesis. HMG-CoA reductase inhibitors are commonly referred to as "statins." Statins are therapeutically effective drugs used for reducing low density lipoprotein (LDL) particle concentration in the blood stream of patients at risk for cardiovascular disease. Rosuvastatin is used in the treatment of hypercholesterolemia (heterozygous familial and nonfamilial) and mixed dyslipidemia (Fredrickson Type IIa and IIb). Rosuvastatin calcium is sold under the brand name CRESTOR®.

U.S. Pat. No. 5,260,440 to Hirai et al. discloses pyrimidine derivatives such as rosuvastatin, its calcium salt (2:1) and its lactone form. The '440 patent also discloses a process for the preparation of pyrimidine derivatives in a four step reaction scheme.

The disadvantages of the prior art include multiple steps resulting in difficult preparations, the use of expensive reagents, reagents that are difficult to use on a commercial scale, the use of low temperatures that make the process more difficult to perform, and time consuming and expensive techniques for purification.

Accordingly, there remains a need for an improved process for the preparation of pyrimidine derivatives such as rosuvastatin that eliminates and reduces the problems of the prior art on a commercial scale in a convenient and cost efficient manner.

SUMMARY OF THE INVENTION

In one embodiment of the present invention, a process for the preparation of pyrimidine derivatives is provided comprising reacting a Wittig reagent of the general formula

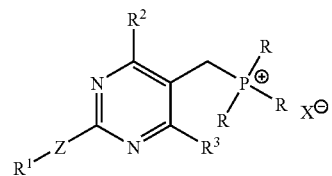

wherein R is an alkyl of from 1 to 10 carbon atoms, aryl or arylalkyl, $R^1$ is a substituted or unsubstituted hydrocarbon group, $R^2$ and $R^3$ are the same or different and are hydrogen or a substituted or unsubstituted hydrocarbon group; Z is sulfur, oxygen, sulfonyl, or imino which may be substituted by formyl, acetyl, propionyl, butyryl, isobutyryl, valeryl, isovaleryl, amino substituted by sulfonyl or alkylsulfonyl, and sulfonyl substituted by alkyl, amino or alkylamino and X is a halogen; with an aldehyde of the general formula

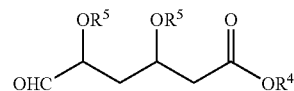

wherein $R^4$ is hydrogen, a lower alkyl or a cation capable of forming a non-toxic pharmaceutically acceptable salt and each $R^5$ are the same or different and are hydrogen or a hydrolyzable protecting group, or each $R^5$, together with the oxygen atom to which each is bonded, form a hydrolyzable cyclic protecting group, or each $R^5$ is bonded to the same substituent which is bonded to each oxygen atom to form a hydrolyzable protecting group; in the presence of a base to provide a pyrimidine derivative of the general formula

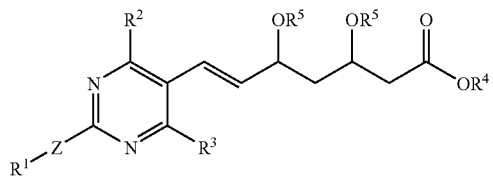

wherein R, $R^1$, $R^2$, $R^3$, $R^4$, $R^5$, X and Z have the aforestated meanings or a racemic mixture, an enantiomer, a diastereoisomer or a mixture thereof.

In a second embodiment of the present invention, a process for the preparation of pyrimidine derivatives comprising reacting a Wittig reagent of the general formula

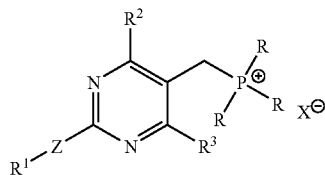

wherein R, $R^1$, $R^2$, $R^3$ Z and X have the aforestated meanings; with an aldehyde of the general formula

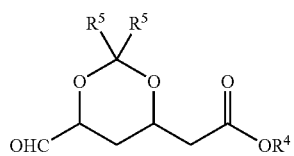

wherein $R^4$ has the aforestated meaning and $R^5$ is a hydrolyzable protecting group; in the presence of a base to provide a pyrimidine derivative of the general formula

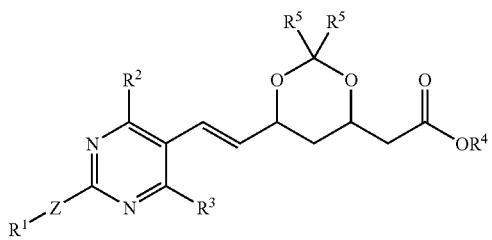

wherein R, $R^1$, $R^2$, $R^3$, $R^4$, $R^5$, and Z have the aforestated meanings or a racemic mixture, an enantiomer, a diastereoisomer or a mixture thereof.

In a third embodiment of the present invention, a process for the preparation of an intermediate of rosuvastatin is provided. The intermediate tert-butyl[E]-(6-{2-[4-(4-fluorophenyl]-6-isopropyl-2-[methyl(methylsulfonyl)amino]pyrimidin-5-yl]vinyl}-(4R,6S)-2,2-dimethyl[1,3]dioxan-4-yl)acetate (BEM) can be prepared by the process comprising reacting a Wittig reagent of the general formula:

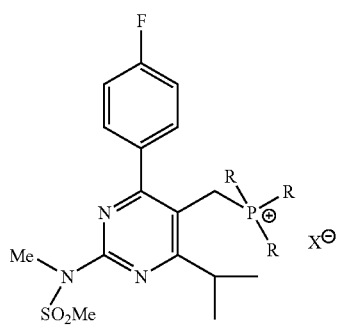

wherein R and X have the aforestated meanings; with tert-butyl-2-[(4R,6S)-6-formyl-2,2-dimethyl-1,3-dioxan-4-yl]acetate (BFA) of the following formula:

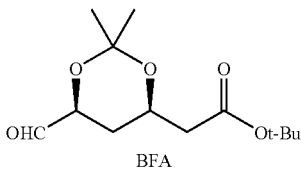

BFA in the presence of a base to provide BEM of the following formula:

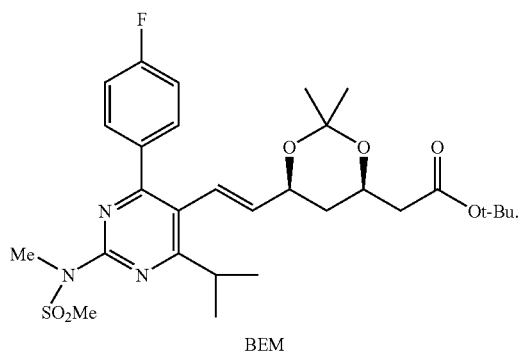

BEM

In a fourth embodiment of the present invention, a process for the preparation of a calcium salt of rosuvastatin is provided comprising:

(a) providing BEM;

(b) contacting the BEM with an amine of the formula $R^6NH_2$, wherein $R^6$ can be an alkyl of from 1 to about 6 carbon atoms in the presence of a dilute acid to form an alkylammonium salt of rosuvastatin; and (c) contacting the alkylammonium salt of rosuvastatin with a sufficient amount of a source of calcium to provide a calcium salt of rosuvastatin.

The advantages of the present invention include:

(1) More economical production on a commercial scale because of the use of inexpensive raw materials, such as triphenyl phosphine and alkali/alkaline earth metal carbonates.

(2) Easier and more economical production on a commercial scale because the reaction conditions are simple, avoid low temperatures, and use a Wittig reagent instead of a Wittig-Horner type reagent.

(3) Higher yields and purity of rosuvastatin and its intermediates.

DETAILED DESCRIPTION OF THE PREFERRED EMBODIMENTS

One aspect of the present invention provides an improved process for the preparation of pyrimidine derivatives, e.g., intermediates of rosuvastatin, of the general Formula I

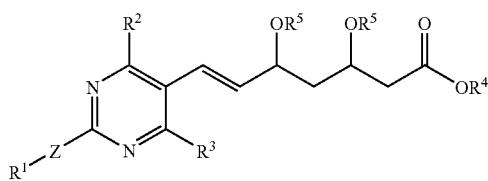

wherein R¹ is a substituted or unsubstituted hydrocarbon group of 1 to about 10 carbon atoms including, by way of example, lower alkyl, aryl or arylalkyl, each of which may have one or more substituents; R² and R³ are the same or different and are hydrogen or a substituted or unsubstituted hydrocarbon group of 1 to about 10 carbon atoms including by way of example, lower alkyl or aryl, each of which may be substituted with one or more substituents; R⁴ is hydrogen, a lower alkyl or a cation capable of forming a non-toxic pharmaceutically acceptable salt; each R⁵ are the same or different and are hydrogen or a hydrolyzable protecting group, or each R⁵, together with the oxygen atom to which each is bonded, form a hydrolyzable cyclic protecting group, or each R⁵ is bonded to the same substituent which is bonded to each oxygen atom to form a hydrolyzable protecting group; and Z is sulfur, oxygen, sulfonyl, or imino which may be substituted by formyl, acetyl, propionyl, butyryl, isobutyryl, valeryl, isovaleryl, amino substituted by sulfonyl or alkylsulfonyl, and sulfonyl substituted by alkyl, amino or alkylamino.

Representative lower alkyls include, but are not limited to, straight, branched, or cyclic $C_1$ to $C_6$ alkyls such as, for example, methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like. The lower alkyls may be substituted with 1 to 3 substituents such as halogens, amino, and cyano. Suitable halogens include, but are not limited to, fluorine, chlorine, bromine, iodine and the like.

Representative aryl groups include, but are not limited to, $C_6$ to $C_{12}$ aromatic group such as, for example, phenyl, tolyl, xylyl, biphenyl, naphthyl, and the like. The aryl groups may be substituted with 1 to 3 substituents such as lower alkyls, halogens, amino, and cyano. A preferred aryl group is phenyl substituted with 1 to 3 halogens.

Representative aralkyl groups include, but are not limited to, $C_1$ to $C_6$ lower alkyls substituted with $C_6$ to $C_{12}$ aromatic aryl groups as defined above. Examples include benzyl, phenethyl, phenylpropyl and the like, each of which may be substituted with 1 to 3 substituents such as lower alkyls, halogens, amino, cyano, and the like.

The term "a cation capable of forming a non-toxic pharmaceutically acceptable salt" refers to alkali metal ions, alkaline earth metal ions, ammonium ions and the like. Examples of alkali metals include lithium, sodium, potassium, and cesium. Examples of alkaline earth metals include beryllium, magnesium, and calcium. Preferred cations are sodium and calcium.

The hydrolyzable protecting groups used are preferably hydrolyzable under acidic or basic conditions. Examples of hydrolyzable protecting groups include, for example, silyl groups such as trialkylsilyl, e.g., t-butyl-dimethyl-silyl, and alkyldiarylsilyl and cyclic protecting groups such that each R⁵ form, for example, a dioxane. In one embodiment, the hydrolyzable protecting group is wherein each R⁵ is bonded to the same substituent which is bonded to each oxygen atom to form a hydrolyzable protecting group, e.g.,

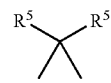

wherein each R⁵ is a lower alkyl as defined above.

The imino may be substituted by formyl, acetyl, propionyl, butyryl, isobutyryl, valeryl, isovaleryl, amino substituted by sulfonyl or alkylsulfonyl wherein the alkyl group has 1 to about 6 carbon atoms, and sulfonyl substituted by alkyl, amino or alkylamino. Examples of aminos substituted with alkylsulfonyls include, but are not limited to, methanesulfonyl amino, ethanesulfonyl amino, propanesulfonyl amino and the like. Examples of substituted sulfonyls as substituent include, but are not limited to, methanesulfonyl, sulfamoyl, methylsulfamoyl, N-dimethylsulfamoyl and the like.

The foregoing pyrimidine derivative can be obtained by reacting a Wittig reagent of the general Formula II:

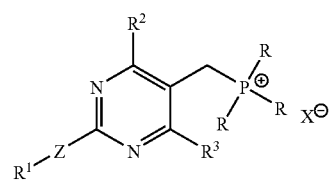

wherein R, R¹, R², R³, Z and X have the aforestated meanings with an aldehyde of the general Formula III

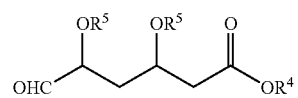

wherein R⁴ and R⁵ have the aforestated meanings; in the presence of a base.

Suitable bases for use herein include, but are not limited to, alkali metal carbonates, e.g., sodium carbonate, potassium carbonate, magnesium carbonate and the like, alkali metal hydroxides and the like and mixtures thereof. Generally, the base is present in the range of about 2.5 to about 4.5 equivalents per equivalent of the Wittig reagent. In another embodiment of the present invention, the base is present in about 3.5 equivalents per equivalent of the Wittig reagent.

In another embodiment of the present invention, the process includes at least reacting the Wittig reagent of Formula IV:

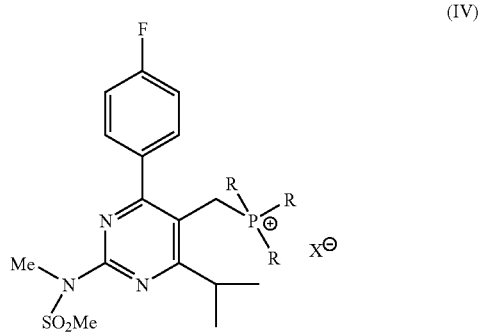

(IV)

wherein R and X have the aforestated meanings, with BFA of Formula V:

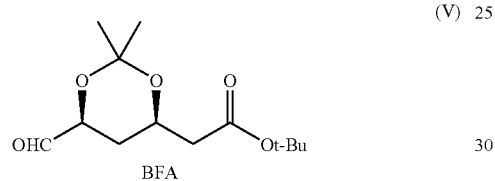

(V)

in the presence of a base to form the compound (BEM) of Formula VI:

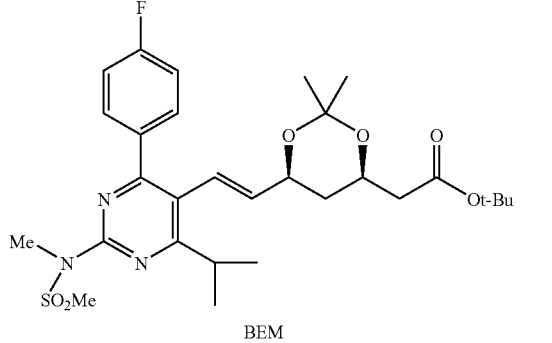

(VI)

a key intermediate in the production of rosuvastatin.

Generally, Wittig reactions are used to convert ketones or aldehydes into alkenes. In these reactions, a phosphorous ylide, $R_2C=P(C_6H_5)_3$ (also called a phosphorane), is added to a ketone or aldehyde, yielding a dipolar intermediate called a betaine. The betaine intermediate of a Wittig reaction decomposes to yield an alkene and a triphenylphosphine oxide. The result is the replacement of carbonyl oxygen by the organic fragment originally bonded to the phosphorous.

In one embodiment of the process of the present invention, the Wittig reagent of Formula II or IV acts as the ylide and reacts with the aldehyde of Formula III or V (e.g., BFA) to yield a pyrimidine derivative (e.g., BEM). Examples of Wittig reagents for use in the process of the present invention include, but are not limited to, triphenyl [4-(4-fluorophenyl)-6-isopropyl-2-[methyl (methylsulfonyl)amino] pyrimidin-5-ylmethyl] phosphonium bromide (TPPBr), tributyl [4-(4-fluorophenyl)-6-isopropyl-2-[methyl(methylsulfonyl)amino]pyrimidin-5-ylmethyl] phosphonium bromide (TBPBr) and the like.

Generally, TPPBr may be prepared by reacting an alcohol of Formula VII:

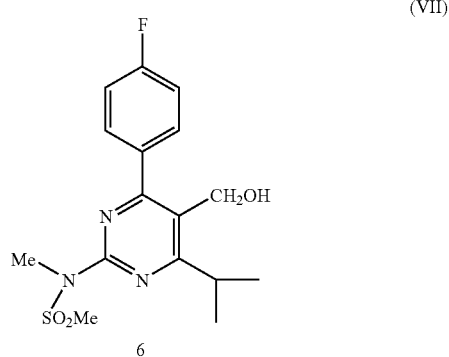

(VII)

with phosphorous tribromide (PBr$_3$) to form a bromide intermediate of Formula VIII:

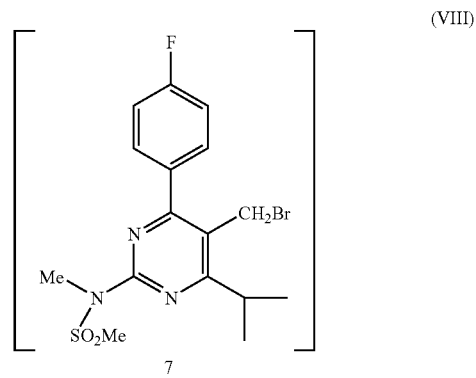

(VIII)

The bromide intermediate is then reacted with triphenyl phosphine to yield TPPBr. The quality and yield of TPPBr depends on how the reagents are added. To obtain the best yields, the bromide intermediate of Formula VI can be added to a preheated triphenyl phosphine (P(Ph)$_3$) preheated to a temperature in the range of from about 80° C. to about 100° C. This results in high quality production of TPPBr.

Generally, TBPBr may be prepared by reacting an alcohol of Formula VII:

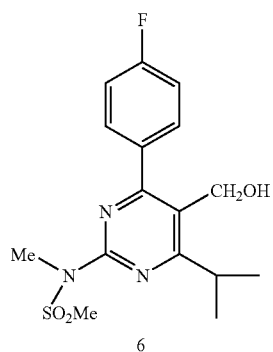

(VII)

with phosphorous tribromide (PBr$_3$) to form a bromide intermediate of Formula VIII:

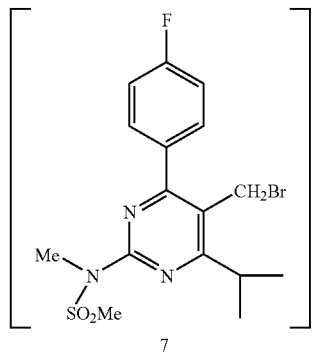

(VIII)

The bromide intermediate is then reacted with tributylphosphine to yield TBPBr.

A preferred aldehyde for use herein is of the general formula

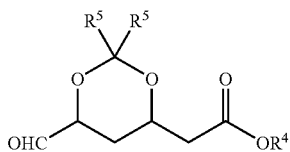

wherein R$^4$ has the aforestated meaning and R$^5$ is a hydrolyzable protecting group such as a lower alkyl as defined hereinabove.

The reaction of the Wittig reagent and aldehyde may be carried out at a temperature ordinarily ranging from about 40° C. to about 90° C., and more preferably at a temperature ranging from about 60° C. to about 80° C. In one embodiment, the aldehyde can be added to the Wittig reagent in an excess amount. In another embodiment, the aldehyde is present in the range of about 1.0 to about 1.3 equivalents per equivalent of the Wittig reagent. The time period for the reaction can range from about 30 minutes to about 3 hours.

If desired, the reaction of the Wittig reagent and aldehyde can be carried out in an aprotic solvent. Suitable aprotic solvents for use in the processes of the present invention include, but are not limited to, dimethylsulfoxide (DMSO), dimethylformamide (DMF), dimethylacetamide (DMA) and the like and mixtures thereof. The solvent can be present in a ratio of Wittig reagent to solvent ordinarily ranging from about 1:3 w/v to about 1:5 w/v.

Following the formation of the Wittig reaction product, the Wittig reaction product can be hydrolyzed by techniques known in the art to provide a pyrimidine derivative such as rosuvastatin as set forth below in Formula IX:

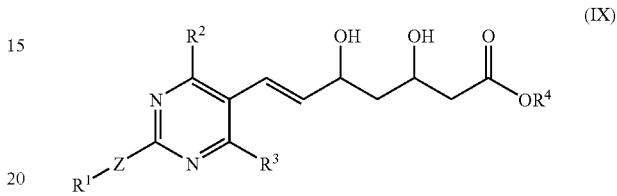

(IX)

wherein R, R$^1$, R$^2$, R$^3$, R$^4$ and Z have the aforestated meanings or a racemic mixture, an enantiomer, a diastereoisomer or a mixture thereof. For example, the Wittig reaction product can be hydrolyzed with a suitable hydrolyzable acid such as, for example, a dilute (about 0.02N to about 1.25N) aqueous mineral acid such as hydrochloric acid at a temperature ranging from about 20° C. to about 60° C., and preferably at a temperature ranging from about 40° C. to about 45° C., for a time period ranging from about 3 to about 6 hours. After the completion of the hydrolysis, the reaction mixture can be cooled and then filtered off, e.g., by crystallization. The wet product can then be dried at a suitable temperature, e.g., about 60° C. to about 65° C., to obtain a substantially pure pyrimidine derivative, e.g., a purity greater than about 90%, preferably greater than about 95% and most preferably greater than about 99%.

As one skilled in the art will readily appreciate, the hydrolyzed pyrimidine derivative of Formula IX can then be converted to a salt such as sodium or calcium salt using techniques known in the art. For example, the hydrolyzed pyrimidine derivative can be converted to a salt using 1N sodium hydroxide solution at room temperature for about 4 to about 5 hours in a suitable solvent medium such as an alcohol solvent, e.g., isopropanol or in a mixture of isopropanol and tetrahydrofuran, in such a manner that there is no free alkali present in the reaction mixture and the sodium salt formation is complete. After stripping the solvent carefully under high vacuum at room temperature, an ether-type solvent, e.g., a dialkyl ether such as diisopropyl ether, can be added and stirred to crystallize out the sodium salt. The sodium salt can be filtered off under totally anhydrous conditions in a dehumidified area and washed with the same or a different solvent to remove slight excess of the ester present.

In another embodiment of the present invention, the pyrimidine derivatives of Formula I can be converted to a pharmaceutically acceptable salt. In one embodiment, the pyrimidine derivative of Formula I can be converted to a pharmaceutically acceptable salt by contacting the pyrimidine derivative with a sufficient amount of a source of calcium, e.g., calcium chloride, calcium acetate and the like, optionally in the presence of at least a suitable hydrolyzable acid such as a dilute (e.g., about 0.02N to about 1.25N) aqueous mineral acid, e.g., hydrochloric acid, (in the case where each $R^5$ is not hydrogen) to produce a calcium salt of the pyrimidine derivative. A "sufficient amount" as used herein refers to the amount of the source of calcium that substantially converts the pyrimidine derivative to the corresponding calcium salt. By "substantially converts" as used herein is meant an amount such that greater than about 50% (molar basis), preferably greater than about 70%, more preferably greater than about 90% and most preferably greater than about 95% of the pyrimidine derivative is converted to the corresponding calcium salt.

In another embodiment of the present invention, the pyrimidine derivatives of Formula I can be converted to a pharmaceutically acceptable salt by first contacting the pyrimidine derivative with an amine source such as an amine of the formula $R^6NH_2$, wherein $R^6$ can be an alkyl of from 1 to about 6 carbon atoms optionally in the presence of at least a suitable hydrolyzable acid such as a dilute (e.g., about 0.02N to about 1.25N) aqueous mineral acid such as hydrochloric acid to produce an alkylammonium salt of the pyrimidine derivative of the general Formula X:

(X)

wherein R, $R^1$, $R^2$, $R^3$, and Z have the aforestated meanings. The reaction can be carried out at a temperature ranging from about −5° C. to about 30° C. for a time period ranging from about 3 to about 5 hours. Generally, the amine source will be present in an amount ranging from about 1.6 to about 1.8 equivalents per equivalent of the pyrimidine derivative. Next, the alkylammonium salt of the pyrimidine derivative of Formula X will be converted to a pharmaceutically acceptable salt by contacting the alkylammonium salt of the pyrimidine derivative with a sufficient amount of a source of calcium, e.g., calcium chloride.

In another embodiment of the present invention, an improved process for the preparation of rosuvastatin is provided including the steps of (a) reacting a Wittig reagent (Formula 1) with BFA (Formula 2) to form BEM (Formula 3); (b) treating the BEM (Formula 3) with hydrochloric acid, sodium hydroxide, sodium chloride, and methylamine to form the methylammonium salt of rosuvastatin (4); and (c) reacting the methylammonium salt of rosuvastatin (4) with calcium chloride to form the calcium salt of rosuvastatin (5). This process is generally depicted in Scheme 1:

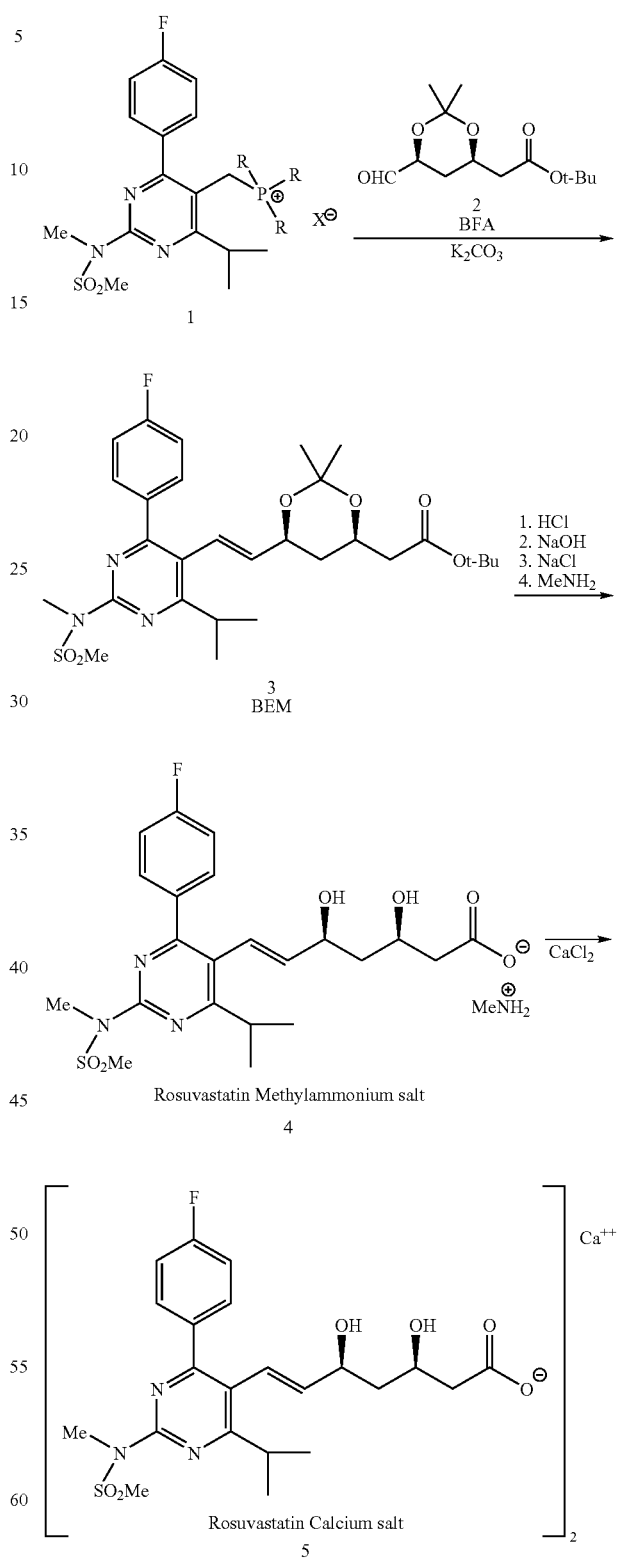

In yet another embodiment of the present invention, rosuvastatin can be prepared as generally depicted in Scheme 2:

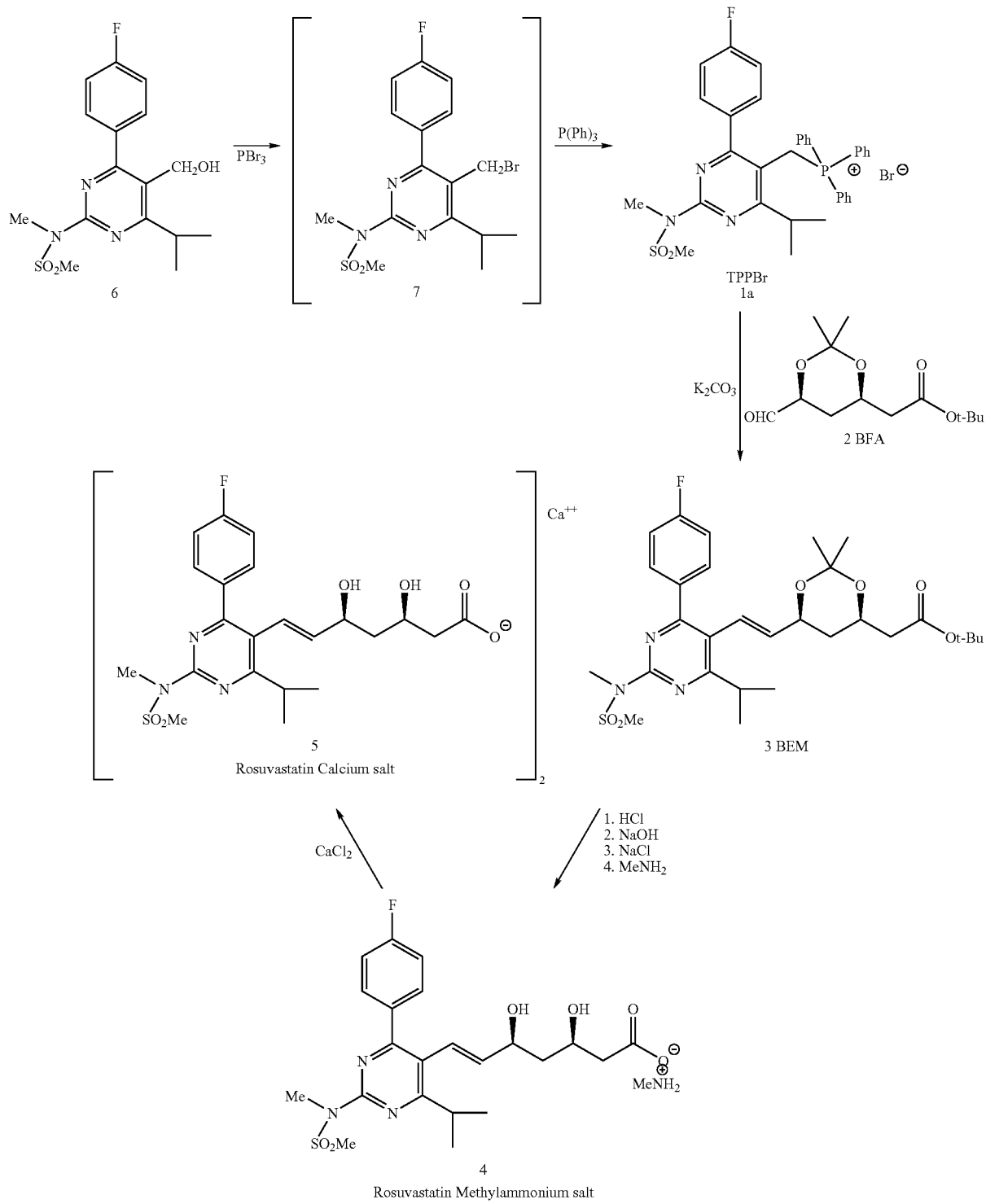

Scheme 2

This process includes the steps of (a) reacting an alcohol of Formula 6 with PBr₃ to form a bromide intermediate (7); (b) reacting the bromide intermediate (7) with P(Ph)₃ to form the Wittig reagent TPPBr (1a); (c) reacting TPPBr (1a) with BFA (2) to form BEM (3); (d) treating the BEM (3) with hydrochloric acid, sodium hydroxide, sodium chloride and methylamine to form the methylammonium salt of rosuvastatin (4); and (e) reacting the methylammonium salt of rosuvastatin (4) with calcium chloride to form the calcium salt of rosuvastatin (5).

In still yet another embodiment of present invention, rosuvastatin can be prepared as generally depicted in Scheme 3:

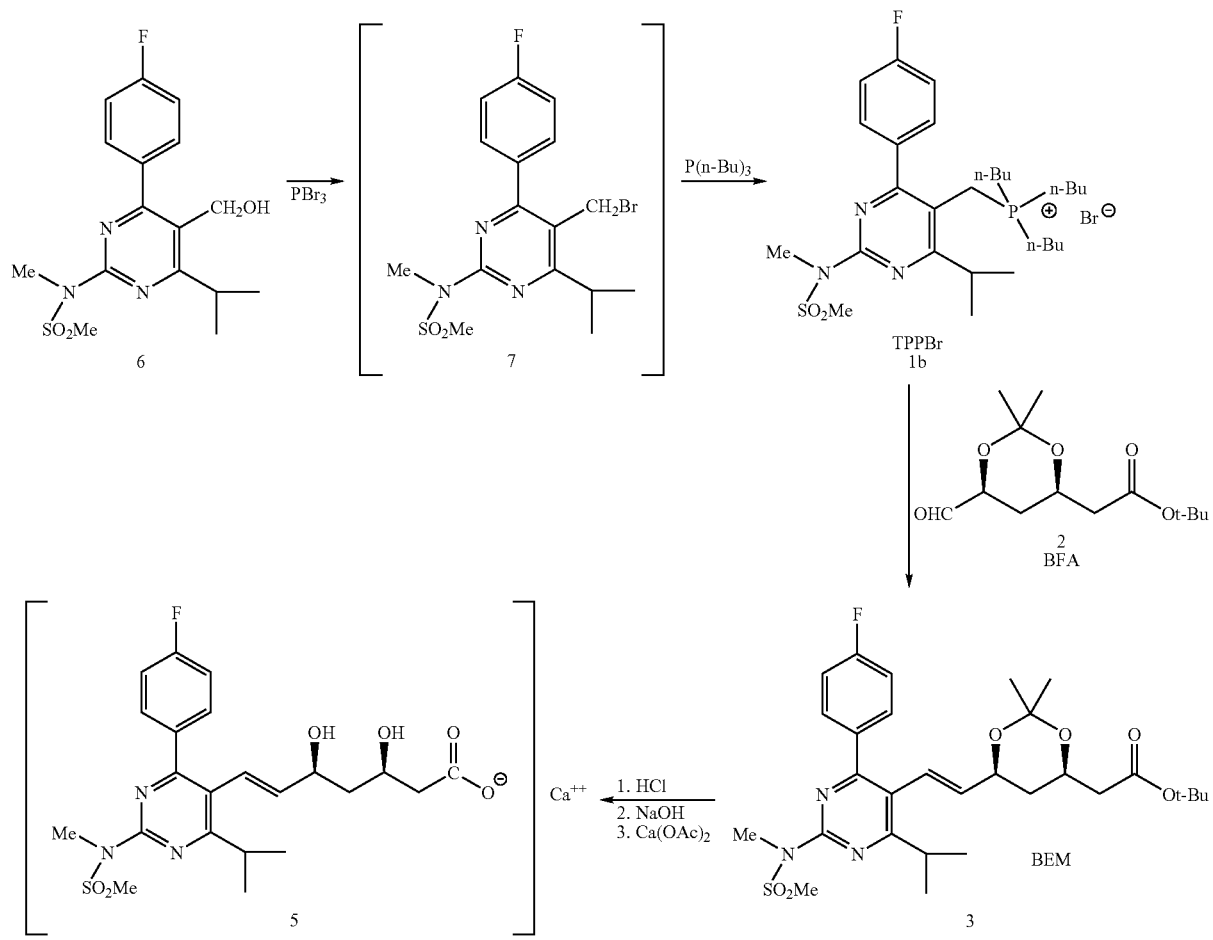

This process comprises the steps of: (a) reacting an alcohol of Formula 6 with PBr$_3$ to form a bromide intermediate (7); (b) reacting the bromide intermediate (7) with P(n-Bu)$_3$ to form the Wittig reagent TBPBr (1b); (c) reacting TBPBr (1b) and BFA (2) to form BEM (3); and (d) treating the BEM (3) with hydrochloric acid, sodium hydroxide, and calcium acetate to form the calcium salt of rosuvastatin (5).

The following examples are provided to enable one skilled in the art to practice the invention and are merely illustrative of the invention. The examples should not be read as limiting the scope of the invention as defined in the claims.

EXAMPLE 1

Preparation of TPPBr

Into a 2 L 4-necked round bottom flask, [4-(4-fluorophenyl)-6-isopropyl-2-(N-methyl-N-methyl sulfonylamino)pyrimidin-5-yl]methanol (100 g), toluene (800 ml) and acetonitrile (400 ml) were added at a temperature in the range of from about 25° C. to about 30° C. under stirring. The reaction mixture was cooled to a temperature of about 15° C. Phosphorous tribromide (35 g) was slowly added over about 30 minutes at a temperature in the range of from about 15° C. to about 20° C. After about 30 minutes, the reaction mixture was added to water (1000 ml) while maintaining the temperature in the range of from about 15° C. to about 20° C. The reaction mixture was stirred for about 5 minutes and the organic layer was separated.

The organic layer was washed with a 10% solution of sodium bicarbonate (500 ml), followed by water (500 ml). The organic layer was concentrated at a temperature in the range of from about 60° C. to about 70° C. under reduced pressure until a distillate (about 800 ml) was collected. The residue was cooled to a temperature of about 60° C. A preheated (ranging from about 80° C. to about 100° C.) mixture of triphenyl phosphine (72 gm) in toluene (500 ml) was added to the residue. The reaction mixture was heated to a temperature of about 110° C. and maintained for about 3 to about 4 hours. After completion of the reaction as determined by TLC, the reaction mixture was cooled to a temperature in the range of from about 20° C. to about 25° C. The precipitated product was filtered, washed with toluene (250 ml), and dried in a vacuum oven at a temperature of below about 60° C. until the moisture content was about 1%. The dried product appears as an off-white crystalline solid weighing about 170 g to about 180 g. The yield was about 88% to about 94%, having a melting point (m.p.) of 238-242° C., and a purity of ~99.5% as determined by HPLC.

The IR (KBr) spectrum shows the absorption bands at 3100 cm$^{-1}$ (C—H str), 2900 (C—H str), 1606 (—C═C-str), 1150 (SO2 str). The $^1$H-NMR (DMSO-d6) shows δ7.89 [m,2H,Ar—H], 7.6-7.4 [m,15H,P(C$_6$H$_5$)3], 7.12 [m,2H, Ar—H], 5.05 [d,1H,CH$_2$P], 3.55-3.75 [2×s,6H,NCH$_3$, SO$_2$CH$_3$], 2.95 [hept,1H,CH(CH$_3$)$_2$], 0.89 [d,6H,CH(CH$_3$)$_2$]. The CI mass shows m/z 600 (base peak). The elemental analysis calculated % C 60.18; % H 5.05; % N 6.19. Observed % C 60.05; % H 5.0, % N 6.0.

EXAMPLE 2

Preparation of TBPBr

Into a 2 L 4-necked round bottom flask, [4-(4-fluorophenyl)-6-isopropyl-2-(N-methyl-N-methyl sulfonyl amino) pyrimidin-5-yl]methanol (100 g), toluene (800 ml) and acetonitrile (400 ml) were added at a temperature in the range of about 25° C. to about 30° C. under stirring. The reaction mixture was cooled to a temperature of about 15° C., and phosphorous tribromide (35 g) was added at a temperature in the range of about 15° C. to about 20° C. slowly over about 30 minutes. Next, the reaction mixture was added to water (1000 ml) over about 30 minutes, while maintaining the temperature in a range of from about 15° C. to about 20° C. The reaction mixture was stirred for 5 minutes at a temperature in the range of from about 15° C. to about 20° C. The organic layer was separated and washed with 10% solution of sodium bicarbonate (500 ml) followed by water (500 ml). The organic layer was concentrated at a temperature in the range of from about 60° C. to about 70° C. under reduced pressure. The white solid obtained was then added to toluene (300 ml) at a temperature of about 25° C. Tri-n-butyl phosphine was then slowly added. After about 20 to about 25 minutes, a bright white solid falls out and is filtered and washed with toluene (100 mL). The solid was then dried in an oven at a temperature below about 50° C. until the moisture content was about 1%. The dried solid appeared as a white crystalline solid weighing about 29 g to about 29.5 g. The yield was about 97% to about 99%, having a mp 180-182° C., and a purity greater than 99% as determined by HPLC.

The IR (KBr) spectrum shows the absorption bands at cm$^{-1}$ 2962 (C—H str), 1604 (—C═C-str), 1155 (SO2 str). The $^1$H-NMR (DMSO-d6) shows δ7.8-7.9[dd,2H,Ar—H], 7.4-7.5[t,2H,Ar—H], 4.0[d,2H,CH$_2$P],3.4-3.5[2×s,6H, NCH$_3$,SO$_2$CH$_3$], 3.41[m,1H,CH(CH$_3$)$_2$], 1.9-2.0[t,6H,P—(CH$_2$)],1.10-1.29[m,18H,—(CH$_2$)$_3$-]0.81[t,9H, (CH$_2$—CH$_3$)$_3$]. The CI mass shows m/z 538.4 (base peak). The elemental analysis calculated % C 54.36; % H 7.49; % N 6.79; Observed % C 54.30; % H 7.41, % N 6.72.

EXAMPLE 3

Preparation of BEM

Into a 2 L 4-necked round bottom flask, DMSO (600 ml), potassium carbonate (104 g), TPPBr (170 g) of Example 1 and BFA (65 g) were added at a temperature in the range of from about 25° C. to about 35° C. under stirring. The reaction mixture was heated to a temperature in the range of from about 70° C. to about 75° C. for about 2 hours. After completion of the reaction as determined by TLC, the reaction mixture was cooled to a temperature in the range of from about 25° C. to about 35° C. Toluene (1000 ml) was added for dilution of the reaction mixture under stirring for about 30 minutes at a temperature in the range of from about 25° C. to about 35° C. The reaction mixture was filtered, and the insoluble cake was separated. The organic layer was added to water (1000 ml) under stirring at a temperature in the range of from about 25° C. to about 35° C. and maintained for about 30 minutes.

The organic layer was separated and washed twice with water (2×1000 ml). The organic layer was distilled in rotavapor bath at a temperature in the range of from about 50° C. to about 70° C. under in a vacuum. After distillation, methanol (750 ml) was added to the residue at a temperature in the range of from about 55° C. to about 60° C. and maintained for about 30 minutes. The reaction mixture was brought to a temperature in the range of from about 25° C. to about 30° C. by slowly circulating water. During this time, a product precipitated out. The precipitated mass was further cooled to a temperature of about 10° C. for about 30 minutes and then filtered. The cake was washed with prechilled methanol (100 ml at a temperature of about 10° C.). The product was dried in an oven at a temperature of about 55 at a temperature of about 10° C. until the moisture content was about 1%. The dried product appeared as an off-white crystalline solid weighing about 108 g to about 110 g. The yield was about 75% to about 76%, having a m.p. of 150-154° C.

The IR (KBr) spectrum shows the absorption bands at 3100 cm$^{-1}$ (C—H str), 2900 (C—H str), 1720 (—COO str), 1605 (—C═C-str), 1150 (SO$_2$str). The $^1$HNMR (CDCl$_3$) TMS as internal standard shows the following signals δ 7.65 [m,2H,Ar—H], 7.09 [m,2H,Ar—H], 6.52 [dd,1H, ArCH═CH], 5.47 [dd,1H,ArCH═CH], 3.57, 3.50 [2×s,6H, NCH$_3$,SO$_2$CH$_3$], 3.38 [hept,1H,Ar—CHMe$_2$], 2.45-2.30 [2×dd,2H,CH$_2$CO$_2$ t-Bu], 1.55, 7.3 [dt,dd,2H,acetonide, CH$_2$], 1.50, 1.40 [2×s,6H,acetonide C(CH$_3$)$_2$], 1.45 [s,9H, CO$_2$C(CH$_3$)$_3$], 1.27 [dd,6H,ArCH(CH$_3$)$_2$]. The CI mass shows m/z 578 (base peak). The elemental analysis shows calculated % C 60.29; % H 6.98; % N 7.27; observed % C 60.12; % H 6.89; % N 7.17.

EXAMPLE 4

Preparation of BEM

In a 250 mL 4-necked round bottom flask, DMSO (150 ml), potassium carbonate (33.54 g), TBPBr (50 g) of Example 2 and BFA (20.87 g) were added at a temperature in the range of about 25° C. to about 35° C. under stirring. The reaction mixture was heated to a temperature of about 70° C. to about 75° C. for about 5 to about 7 hours. After the completion of the reaction as determined by TLC, the reaction mixture was cooled to a temperature in the range of about 25° C. to about 35° C. Toluene (250 ml) was added for dilution of the reaction mixture and stirred for about 30 minutes. The organic layer was added to water (100 ml) under stirring and maintained for 30 minutes. The organic layer was separated and washed with water (2×100 ml) in the same manner as described above. The organic layer was distilled in Rota vapor bath at temperature in the range of from about 50° C. to about 60° C. under vacuum. After distillation, IPA (100 ml) was added to the residue at a temperature of about 55° C. to about 60° C. and the mixture was maintained for about 30 minutes. The reaction mixture was brought to a temperature in the range of from about 25° C. to about 30° C. by Circulating room temperature water slowly. In this period, the product precipitates and the precipitated mass was further cooled to a temperature of about 10° C. for about 30 minutes, and then filtered. The cake was washed with prechilled (at a temperature of about 10° C.) IPA (50 ml). The product was dried in an oven at a temperature of about 55° C. until the moisture content was about 1%. The dried product appeared as an off-white crystalline solid weighing about 44 g to about 45 g. The yield was about 88% to about 90%, and having a m.p. of 150-154° C.

The IR (KBr) spectrum shows the absorption bands at 3100 cm$^{-1}$ (C—H str), 2900 (C—H str), 1720 (—COO str), 1605 (—C═C-str), 1150 (SO$_2$str). The $^1$HNMR (CDCl$_3$) TMS as internal standard shows the following signals δ 7.65 [m,2H,Ar—H], 7.09 [m,2H,Ar—H], 6.52 [dd,1H,ArCH═CH], 5.47 [dd,1H,ArCH═CH], 3.57, 3.50 [2×s,6H, NCH$_3$,SO$_2$CH$_3$], 3.38 [hept,1H,Ar—CHMe$_2$], 2.45-2.30 [2×dd,2H,CH$_2$CO$_2$t-Bu], 1.55, 7.3 [dt,dd,2H,acetonide,CH$_2$], 1.50, 1.40 [2×s,6H,acetonideC(CH$_3$)$_2$], 1.45 [s,9H, CO$_2$C(CH$_3$)$_3$], 1.27 [dd,6H,ArCH(CH$_3$)$_2$]. The CI mass shows m/z 578 (base peak). The elemental analysis shows calculated % C 60.29; % H 6.98; % N 7.26; observed % C 60.17; % H 6.93; % N 7.21.

EXAMPLE 5

Preparation of Rosuvastatin Methylammonium Salt

Into a 2 L 4-necked round bottom flask, BEM (100 g) of Example 4 and acetonitrile (700 ml) were added and stirred under an inert atmosphere at about 40° C. Next, 0.02M hydrochloric acid (190 ml) was added to the reaction mixture over about 30 minutes while maintaining the temperature in the range of from about 35° C. to about 40° C. The mixture was stirred at a temperature of about 40° C. for about 3 hours. After completion of the reaction as determined by TLC, the reaction mixture was cooled to a temperature of about 25° C. 1.0 M sodium hydroxide solution (190 ml) was added to the reaction mixture under stirring and the mixture was stirred for an additional one hour. After completion of the reaction as determined by TLC, sodium chloride (94 g) was added and the mixture was cooled to a temperature of about −5° C. for about 1 hour.

A solution of 1M HCl (190 ml) and sodium chloride (48 g) were added at a temperature of about −5° C. to achieve a pH in the range of from about 3.4 to about 4. The mixture was stirred for about 5 to about 10 minutes. The mixture was allowed to settle for about 10 minutes at a temperature of about −5° C., resulting in two layers. The bottom layer was separated and discarded. Acetonitrile (1.3 L) was added to the remaining solution at a temperature of about −5° C. The mixture was filtered through a hyflow bed. A 40% methylamine solution (24 ml) was added at a temperature of about −5° C. The mixture was then warmed to a temperature of about 30° C. over about 40 minutes and maintained for about 90 minutes. The mixture was then cooled to a temperature of about 0° C. over about 40 minutes and maintained for about 90 minutes. The resulting solid was filtered and washed twice with acetonitrile (2×200 ml). The isolated solid is the methylamine salt of the rosuvastatin. It was dried at a temperature in the range of from about 35° C. to about 45° C. under a vacuum. The dried product appeared as an off-white crystalline solid weighing about 65 g to about 75 g. The yield was about 71% to about 84%, having a purity of 99% (HPLC) and a m.p. of 154-160° C.

The IR (KBr) spectrum shows the absorption bands at 3540-3400 cm$^{-1}$ (O—H, N—H str), 3100 (C—H str), 2900 (C—H str), 1660(—COO— str), 1605 (—C═C— str), 1150 (SO$_2$str). The $^1$H-NMR (CDCl$_3$) TMS as internal standard shows the following signals δ 7.7 (2H,t), 7.3 (2H,t), 6.5 (1H,d), 5.5 (1H,dd), 4.2(1H,m), 3.8(1H,m), 3.4(6H,s), 3.5 (3H,s), 1.9-2.1(2H,dd), 1.3-1.5 (2H,m), 1.2 (6H,d). The CI Mass shows m/z 482 (base peak). The elemental analysis shows calculated % C 53.89; % H 6.49; % N 10.93, and observed % C 53.72; % H 6.38; % N 10.80.

EXAMPLE 6

Preparation of Rosuvastatin Calcium Salt

Into a 2 L 4-necked round bottom flask, rosuvastatin methylammonium salt (10 g) of Example 5 and demineralized water (500 m) were added at a temperature of about 20° C. under stirring. Aqueous sodium hydroxide solution (8% w/w, 90.6 ml) was added at a temperature of about 20° C. under stirring for about 1 hour. The mixture was filtered and concentrated at a temperature below about 40° C. under reduced pressure. A distillate (about 400 ml) was collected. Demineralized water (400 ml) was added and the mixture was again concentrated under reduced pressure at a temperature of about 40° C. A distillate (about 400 ml) was collected. Demineralized water (500 ml) was added to the residue, followed by dropwise addition of a solution of calcium chloride dihydrate (17.16 g) in demineralized water (103 ml) at a temperature of about 20° C. The mixture was stirred for about 45 minutes at and a solid was precipitated. The solid was filtered, washed with water (600 ml), and dried under vacuum until the moisture content was about 3.5% to about 5% at a temperature of about 40° C. The dried product was the calcium salt of rosuvastatin and appeared as an off-white crystalline solid weighing about 80 g to about 85 g. The yield was about 79% to about 84%, having a purity of 99% (HPLC).

The specific optical rotation α D 20=+15-16° (C=0.5% in MeOH). The DSC shows two broad endotherms. The first endotherm shows a peak temperature of 85.76° C. (onset temp 63.6° C. corresponding to the water). The second endotherm shows a peak temperature of 225° C. (onset temperature 198° C.). The IR (KBr) spectrum shows the absorption bands at 3500-3400 cm$^{-1}$ (O—H str), 3100 (C—H str), 2900 (C—H str), 1704 (—COO-str), 1605 (—C═C-str), 1150 (SO$_2$ str). The $^1$HNMR (CDCl$_3$) TMS as internal standard shows the following signals δ 7.7 (2H,t), 7.3 (2H,t), 6.5 (1H,d), 5.5 (1H,dd), 4.2(1H,m), 3.8(1H,m), 3.5(3H,s), 1.9-2.1(2H,dd), 1.3-1.5 (2H,m), 1.2 (6H,d). The CI Mass shows m/z 482 (base peak). The elemental analysis shows calculated % C 50.76; % H 5.23; % N 8.07; and observed % C50.58; % H 5.15; % N 7.8.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for the preparation of pyrimidine derivatives comprising reacting a Wittig reagent of the general formula

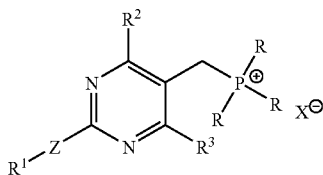

wherein R is an alkyl of from 1 to 10 carbon atoms, aryl or arylalkyl, $R^1$ is a substituted or unsubstituted hydrocarbon group, $R^2$ and $R^3$ are the same or different and are hydrogen or a substituted or unsubstituted hydrocarbon group; Z is sulfur, oxygen, sulfonyl, or imino which may be substituted by formyl, acetyl, propionyl, butyryl, isobutyryl, valeryl, isovaleryl, amino substituted by sulfonyl or alkylsulfonyl, and sulfonyl substituted by alkyl, amino or alkylamino and X is a halogen; with an aldehyde of the general formula

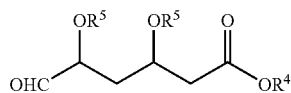

wherein $R^4$ is hydrogen, a lower alkyl or a cation capable of forming a non-toxic pharmaceutically acceptable salt and each $R^5$ are the same or different and are hydrogen or a hydrolyzable protecting group, or each $R^5$, together with the oxygen atom to which each is bonded, form a hydrolyzable cyclic protecting group, or each $R^5$ is bonded to the same substituent which is bonded to each oxygen atom to form a hydrolizable protecting group; in the presence of a base to provide a pyrimidine derivative of the general formula

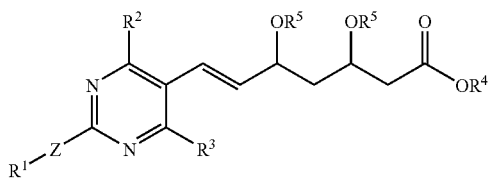

wherein R, $R^1$, $R^2$, $R^3$, $R^4$, $R^5$, X and Z have the aforestated meanings or a racemic mixture, an enantiomer, a diastereoisomer or a mixture thereof.

2. The process of claim 1, wherein $R^1$ is a substituted or unsubstituted hydrocarbon group of 1 to about 10 carbon atoms, $R^2$ and $R^3$ are the same or different and are a substituted or unsubstituted hydrocarbon group of 1 to about 10 carbon atoms and $R^4$ is a lower alkyl of 1 to 6 carbon atoms.

3. The process of claim 1, wherein $R^1$ is selected from the group consisting of lower alkyl which may have 1 to 3 substitutents independently selected from the group consisting of halogen, amino, and cyano, a $C_6$ to $C_{12}$ aromatic group which may have 1 to 3 substituents independently selected from the group consisting of lower alkyl, halogen, amino, and cyano, and $C_1$ to $C_6$ lower alkyl substituted by $C_6$ to $C_{12}$ aromatic group which may have 1 to 3 substituents independently selected from the group consisting of lower alkyl, halogen, amino, and cyano; $R^2$ is a lower alkyl which may have 1 to 3 substituents independently selected from the group consisting of halogen, amino, and cyano, or a $C_6$ to $C_{12}$ aromatic group which may have 1 to 3 substituents independently selected from the group consisting of lower alkyl, halogen, amino, and cyano; $R^3$ is a lower alkyl which may have 1 to 3 substituents independently selected from the group consisting of halogen, amino, and cyano, $R^4$ is hydrogen or a lower alkyl which may have 1 to 3 substituents independently selected from the group consisting of halogen, amino, and cyano.

4. The process of claim 1, wherein $R^1$ is a lower alkyl of 1 to 6 carbon atoms; $R^2$ is a $C_6$ to $C_{12}$ aromatic group which may have 1 to 3 substituents independently selected from the group consisting of lower alkyl, halogen, amino, and cyano; $R^3$ is a lower alkyl of 1 to 6 carbon atoms, $R^4$ is a lower alkyl of 1 to 6 carbon atoms.

5. The process of claim 1, wherein Z is an amino substituted by sulfonyl or alkylsulfonyl wherein the alkyl group contains from 1 to 6 carbon atoms.

6. The process of claim 1, wherein Z is methanesulfonyl amino.

7. The process of claim 1, wherein the Wittig reagent is triphenyl [4-(4-fluorophenyl)-6-isopropyl-2-[methyl(methylsulfonyl)amino]pyrimidin-5-ylmethyl] phosphonium bromide or tributyl [4-(4-fluorophenyl)-6-isopropyl-2-[methyl (methylsulfonyl)amino]pyrimidin-5-ylmethyl] phosphonium bromide and the aldehyde is of the general formula

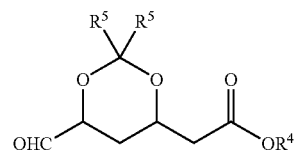

wherein $R^4$ has the aforestated meaning and each $R^5$ is the same or different and is a lower alkyl group.

8. The process of claim 1, wherein the base is selected from the group consisting of alkali metal carbonates, alkali metal hydroxides and mixtures thereof.

9. The process of claim 1, wherein the base is an alkali metal carbonate selected from the group consisting of sodium carbonate, potassium carbonate, magnesium carbonate and mixtures thereof.

10. The process of claim 1, wherein the reaction is carried out at a temperature of about 40° C. to about 90° C.

11. The process of claim 1, wherein the reaction is carried out at a temperature of about 60° C. to about 80° C.

12. The process of claim 1, wherein the base is present in an amount of about 2.5 to about 4.5 equivalents per equivalent of the Wittig reagent.

13. The process of claim 1, wherein the base is present in an amount of about 3.5 equivalents per equivalent of the Wittig reagent.

14. The process of claim 1, wherein the aldehyde is added to the Wittig reagent in an excess amount.

15. The process of claim 1, wherein the aldehyde is present in an amount of about 1 to about 1.3 equivalents per equivalent of the Wittig reagent.

16. The process of claim 1, wherein the reaction is carried out in one or more aprotic solvents.

17. The process of claim 16, wherein the aprotic solvent is selected from the group consisting of dimethyl sulfoxide, dimethylformamide, dimethylacetamide and mixtures thereof.

18. The process of claim 16 wherein the solvent is present in a ratio of Wittig reagent to solvent of about 1:3 w/v to about 1:5 w/v.

19. The process of claim 1, further comprising hydrolyzing the pyrimidine derivative to produce a hydrolyzed pyrimidine derivative of the general formula:

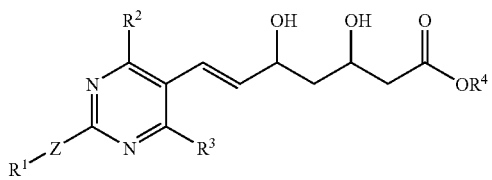

wherein R, $R^1$, $R^2$, $R^3$, $R^4$ and Z have the aforestated meanings or a racemic mixture, an enantiomer a diastereoisomer or a mixture thereof.

20. The process of claim 19, wherein the step of hydrolyzing the pyrimidine derivative comprises contacting the pyrimidine derivative with a dilute acid.

21. The process of claim 20, wherein the dilute acid is hydrochloric acid.

22. The process of claim 19, wherein the hydrolyzed pyrimidine derivative is converted to a pharmaceutically acceptable salt of the pyrimidine derivative.

23. The process of claim 19, wherein the hydrolyzed pyrimidine derivative is converted to a calcium salt of the pyrimidine derivative.

24. The process of claim 19, wherein the hydrolyzed pyrimidine derivative is purified.

25. The process of claim 1, wherein the pyrimidine derivative is converted to a pharmaceutically acceptable salt of the pyrimidine derivative.

26. The process of claim 1, wherein the pyrimidine derivative is converted to a calcium salt of the pyrimidine derivative.

27. The process of claim 1, wherein the pyrimidine derivative is contacted with a sufficient amount of a source of calcium in the presence of a dilute acid to provide a calcium salt of the pyrimidine derivative.

28. The process of claim 1, wherein the pyrimidine derivative is contacted with a sufficient amount of a calcium acetate in the presence of a dilute acid to provide a calcium salt of the pyrimidine derivative.

29. The process of claim 1, further comprising contacting the pyrimidine derivative with an amine of the general formula $R^6NH_2$ wherein $R^6$ is an alkyl of from 1 to about 6 carbon atoms in the presence of a dilute acid to produce an alkylammonium salt of the pyrimidine derivative of the general formula:

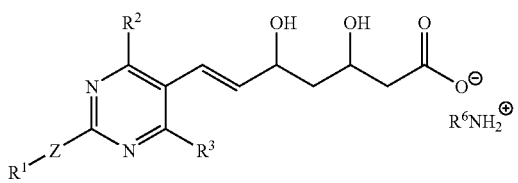

wherein R, $R^1$, $R^2$, $R^3$, and Z have the aforestated meanings.

30. The process of claim 29, wherein the dilute acid is hydrochloric acid.

31. The process of claim 29, wherein the amine is present in an amount of from about 1.6 to about 1.8 equivalents per equivalent of the pyrimidine derivative.

32. The process of claim 29, wherein the alkylammonium salt of the pyrimidine derivative is converted to a pharmaceutically acceptable salt.

33. The process of claim 32, wherein the pharmaceutically acceptable salt is a calcium salt of the pyrimidine derivative.

34. The process of claim 29, further comprising contacting the alkylammonium salt of the pyrimidine derivative with a sufficient amount of a source of calcium to provide a calcium salt of the pyrimidine derivative.

35. The process of claim 29, further comprising contacting the alkyl ammonium salt of the pyrimidine derivative with a sufficient amount of calcium chloride to provide a calcium salt of the pyrimidine derivative.

36. The process of claim 1, further comprising contacting the pyrimidine derivative with an amine of the general formula $R^6NE_2$ wherein $R^6$ can be an alkyl of from 1 to about 6 carbon atoms in the presence of a dilute acid to produce an alkylammonium salt of the pyrimidine derivative of the general formula:

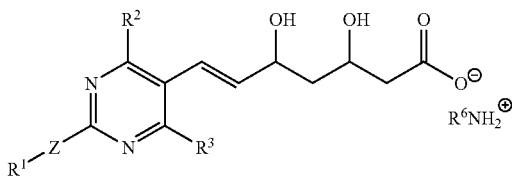

wherein R, $R^1$, $R^2$, $R^3$, and Z have the aforestated meanings; and contacting the alkylammonium salt of the pyrimidine derivative with a sufficient amount of calcium chloride to provide a calcium salt of the pyrimidine derivative.

37. The process of claim 36, wherein the amine is present in an amount of about 1.6 to about 1.8 equivalents per equivalent of the pyrimidine derivative.

38. A process for the preparation of tert-butyl[E]-(6-{2-[4-(4-fluorophenyl)-6-isopropyl-2-[methyl(methylsulfonyl)amino]pyrimidin-5-yl]vinyl}-(4R,6S)-2,2-dimethyl[1,3]dioxan-4-yl)acetate (BEM) comprising reacting a Wittig reagent of the general formula:

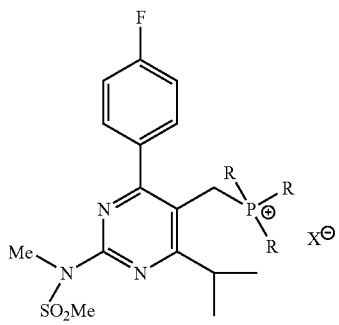

wherein R is the same or different and can be an alkyl of from 1 to 10 carbon atoms, aryl or an arylalkyl and X is a halogen, with tert-butyl-2-[(4R,6S)-6-formyl-2,2-dimethyl-1,3-dioxan-4-yl]acetate (BFA) of the general formula

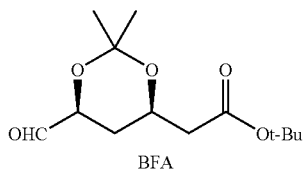
BFA in the presence of a base.

39. The process of claim 38, wherein the Wittig reagent is triphenyl [4-(4-fluorophenyl)-6-isopropyl-2-[methyl(methylsulfonyl)amino]pyrimidin-5-ylmethyl] phosphonium bromide.

40. The process of claim 38, wherein the Wittig reagent is tributyl [4-(4-fluorophenyl)-6-isopropyl-2-[methyl(methylsulfonyl)amino]pyrimidin-5-ylmethyl] phosphonium bromide.

41. The process of claim 38, wherein the reaction is carried out at a temperature of about 40° C. to about 90° C.

42. The process of claim 38, wherein the reaction is carried out at a temperature of about 60° C. to about 80° C.

43. The process of claim 38, wherein the base is present in an amount of about 2.5 to about 4.5 equivalents per equivalent of the Wittig reagent.

44. The process of claim 38, wherein the base is present in an amount of about 3.5 equivalents per equivalent of the Wittig reagent.

45. The process of claim 38, wherein BFA is present in an amount of about 1.0 to about 1.3 equivalents per equivalent of the Wittig reagent.

46. The process of claim 38, wherein the base is selected from the group consisting of sodium carbonate, potassium carbonate, magnesium carbonate and mixtures thereof.

47. The process of claim 38, wherein the reaction is carried out in the presence of one or more aprotic solvents.

48. The process of claim 47, wherein the solvent is selected from the group consisting of dimethyl sulfoxide, dimethylformamide, dimethylacetamide and mixtures thereof.

49. The process of claim 38, further comprising converting BEM to a calcium salt of rosuvastatin.

50. The process of claim 49, wherein the step of converting comprises contacting BEM with a sufficient amount of a source of calcium in the presence of a dilute acid to provide the calcium salt of rosuvastatin.

51. The process of claim 49, wherein the step of converting comprises contacting BEM with a sufficient amount of calcium acetate in the presence of a dilute acid to provide the calcium salt of rosuvastatin.

52. A process for the preparation of a rosuvastatin salt comprising the steps of:

(a) reacting a Wittig reagent of the general formula:

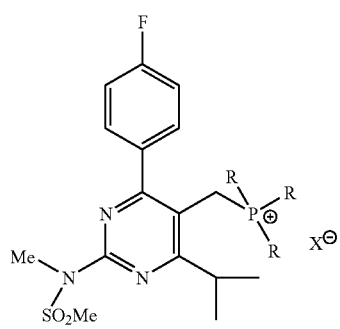

wherein R is an alkyl of from 1 to 10 carbon atoms, aryl or arylalkyl and X is a halogen, with BFA in the presence of a base to form BEM; and (b) converting BEM to a salt of rosuvastatin.

53. The process of claim 52, wherein the salt is the calcium salt of rosuvastatin.

54. A compound of the general formula

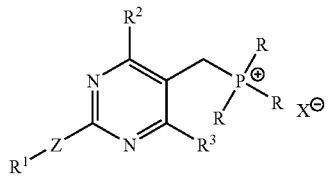

wherein R is an alkyl of from 1 to 10 carbon atoms, aryl or arylalkyl, $R^1$ is a substituted or unsubstituted hydrocarbon group, $R^2$ and $R^3$ are the same or different and are hydrogen or a substituted or unsubstituted hydrocarbon group; Z is sulfur, oxygen, sulfonyl, or imino which may be substituted by formyl, acetyl, propionyl, butyryl, isobutyryl, valeryl, isovaleryl, amino substituted by sulfonyl or alkylsulfonyl, and sulfonyl substituted by alkyl, amino or alkylamino and X is a halogen.

55. The compound of claim 54, which is of the formula:

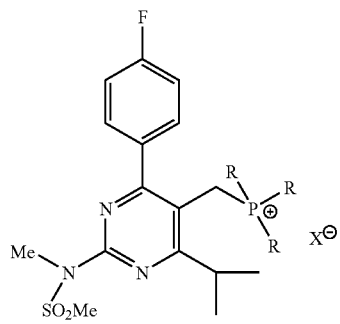

wherein R and X have the aforestated meanings.

* * * * *